United States Patent [19]

Madsen

[11] 4,322,207
[45] Mar. 30, 1982

[54] DENTAL CLEANING SLURRY

[76] Inventor: Erik H. Madsen, 2405 Camino Way, Salt Lake City, Utah 84121

[21] Appl. No.: 652,566

[22] Filed: Jan. 26, 1976

[51] Int. Cl.³ .............................................. A61K 5/00
[52] U.S. Cl. ..................................... 433/216; 433/125
[58] Field of Search ...................... 32/57; 51/293, 328, 51/317; 424/49, 52

[56] References Cited

U.S. PATENT DOCUMENTS

| 1,664,369 | 3/1928 | Maurer | 32/58 |
| 2,820,000 | 1/1958 | Menzies | 424/49 |
| 3,344,524 | 10/1967 | Kulischenko | 32/58 |
| 3,593,707 | 7/1971 | Pifer | 128/66 |
| 3,778,517 | 12/1973 | Neely | 424/49 |
| 3,937,806 | 2/1976 | Cooley | 424/49 |

FOREIGN PATENT DOCUMENTS 1331249 9/1973 United Kingdom .................... 32/58

OTHER PUBLICATIONS

"Notes on Dental Materials" by Canbe MSC, Phd, ARIC, Chapter 30, p. 237, printed by Unwiw Bros., Ltd., Old Woking Surrey, England.

Primary Examiner—Robert Peshock
Attorney, Agent, or Firm—B. Deon Criddle

[57] ABSTRACT

A dental cleaning slurry and method of cleaning teeth comprising an aqueous suspension of particulate material having a hardness which is softer than the softest exposed part of the teeth. The slurry is directed against the teeth under sufficient water pressure for the particulate material to penetrate and dislodge any plaque or food particles that may adhere to the teeth.

13 Claims, No Drawings

DENTAL CLEANING SLURRY

BACKGROUND OF THE INVENTION

This invention relates to a tooth cleaning slurry. More particularly, this invention relates to a tooth cleaning slurry containing small particulate materials which aid in the removal of foreign substances adhering to the teeth.

Traditionally, teeth have been cleaned by using a toothbrush with the aid of toothpaste or toothpowder. Toothpaste and powder have the same basic composition, both contain a mildly abrasive substance such as a finely powdered calcium carbonate and a detergent or soaplike material. However, such cleaning compositions are abrasive to the teeth and gradually wear away the enamel and/or cementum which form the outer part of the tooth. Although enamel is the hardest material in the human body and covers the crown of the tooth, it may be still worn away by abrasives.

On the other hand, if teeth are not properly taken care of, food substances lodge between the teeth and plaque, a gelatinous accumulation of bacteria and salivary mucin, form on the teeth.

Daily cleansing of the teeth is essential to keep the teeth clean and the gums stimulated and firm. The lack of proper cleansing of the teeth causes the bacteria living on the exposed surfaces of the teeth to cause food particles to ferment, which fermentation forms an acid that destroys the tooth enamel. After tooth enamel has been destroyed, the dentin underlying enamel is also attacked, and cavities are formed.

Within the past several years, alternatives to the toothbrush have been developed which usually take the form of a water spray directed against the teeth. While the water is not abrasive to the teeth as are the materials found in toothpaste, a thorough cleaning job is still not obtained.

It is an object of the present invention to provide a cleaning composition that will effectively remove plaque and food particles, but which is not abrasive to the teeth.

it is a further object of this invention to provide a slurry for the cleaning of teeth whereby the slurry contains particulate particles which are softer than the surface of the teeth but which effectively remove plaque and food particles.

It is a still further object of the present invention to provide a method of cleaning teeth utilizing an aqueous slurry of particulate materials which are softer than the surface of the teeth.

DETAILED DESCRIPTION OF THE INVENTION

These and other objects are accomplished by means of a novel toothcleaning composition comprising an aqueous slurry of a particulate material suspended in water wherein the particulate material has a hardness which is considerably softer than the cementum or softest exposed portion of the tooth. The particulate particles are insoluble in the slurry. The volume of particulate material to water in the slurry should be on the order of from 1:1.5 to 1:10. Preferably, volumetric ratios of particulate material to water of from 1:4 to 1:6 are used with the preferred ratios being 1:5. If preferred the slurry can be prepared as a concentrate and later diluted for use.

As previously stated, the particles contained within the slurry should have a surface hardness which is softer than the softest exposed part of the tooth, i.e., the dentin which is softer than both the enamel covering the crown of the tooth and the cementum, which is the layer that is found relative to the surface of a root of the tooth. The dentin is a hard calcareous tissue similar to but denser than bone, and it forms the major portion of the tooth. The particles, therefore, should have a hardness measured on the Knoop Scale that is less than 68. The Knoop Scale of hardness is a standard test based on the indentation made in the material to be tested by a diamond point.

The particle size of the materials is preferably between about 0.002 inches and 0.020 inches; while the particles can be round, it is preferred that they be irregular in shape in order to more effectively remove the plaque and food particles from the teeth. The size of the particles is important to make sure that, at the pressure delivered, the particles will have sufficient momentum to penetrate the aqueous boundary layers surrounding the teeth, such penetration being sufficiently forceful to dislodge any plaque or food particles that may be located on the tooth surface. The particles therefore, are delivered through an orifice in a pressure range which is preferably between about 15 to 60 pounds per square inch with ranges of about 30 to 40 pounds per square inch being preferred.

The particulate materials utilized should be inert and will not sustain a growth of carcinogenic microorganisms or any organisms that may produce or sustain gingivitis, i.e., inflamation of the gums.

Preferred particulate materials which may be utilized include conventionally available plastic such as polymers and copolymers of both a thermoplastic and thermosetting variety with thermoplastic polymers being especially preferred. Thermoplastic polymers may include plasticized or unplasticized materials such as polypropylene and polyethylene, polyvinylchloride, polystyrene, polyurethane, polyethylenepolyvinyl acetate copolymers, polyesters and the like.

Other naturally occurring or synthetic materials may be used as well since the criticality resides in the hardness of the particulate material and not in its chemical composition. Therefore, any inert non-toxic material may be used. Exemplary of materials other than plastics are materials comminuted to a proper size including sawdust, hemp, sisal, seeds, cereal grains, natural and synthetic rubbers, metals and the like.

The slurry as defined herein is suitable for the cleaning of teeth in the place of the usual toothbrush and may contain added ingredients commonly found in toothpaste if desired. For example, the slurry may contain a breath sweetener such as oil of peppermint or oil of wintergreen. In addition to this, disinfectants such as cetylpyridium chloride, zinc chlorides of sodium phenolate may be used. It is also possible to simultaneously treat the teeth with a floride such as adding sodium fluoride or monofluorophosphate to the slurry. Any breath sweetener, disinfectant, or fluoridating agent will be water soluble and will therefore not affect the ratio of plastic to aqueous solution. The concentrations of breath sweeteners, disinfectants, and fluoridating agents may be those conventionally used in toothpastes and are not critical to the present invention. They will, in general, vary from about 0.05 to 3% by weight.

The slurry is directed against the teeth through an orifice attached to a flexible hose. Various devices are known in the art for directing a stream of water into the oral cavity for the cleansing of teeth and the like. However, for handling hygienic slurries as claimed herein, the apparatus disclosed in my copending application, serial No. 470,365 filed May 16, 1974 and now U.S. Pat. No. 3,971,136 issued July 27, 1976, incorporated herein by reference, is preferred. The size of the orifice is such that the slurry particles may freely move therethrough without obstructing or plugging of the orifice. The slurry particles must be moved with sufficient force to dislodge the plaque or food particles adhering to the surface of the teeth. In general, it has been found that pressures ranging from about 15 to 60 psi may be utilized with pressures ranging from about 30 to 40 psi being preferred.

Such hygienic slurries are adaptable for use at home, in the school, in dental offices, hospitals and the like. The slurry can be systematically applied as a jet or pressurized stream to tooth areas enabling the plaque and food particles to be dislodged thereby providing a high degree cleaning to the teeth. Areas which are hard to reach by brush bristles can be easily and efficiently cleaned when contacted by the slurry as has been described.

Since the materials used are nontoxic, there is no danger to the user if a portion of the slurry is swallowed. However, preferably, the slurry solution will be evacuated from the mouth or expectorated. If desired, the particulate matter may be filtered from the slurry after use and disinfected for reuse. The particles spent can be collected by filter paper and the like and appropriately disinfected with disinfectant solutions such as ethyl or isopropyl alcohol, or chlorinated ammonium compounds.

What is claimed is:

1. A hygienic slurry for the cleaning of teeth comprising an aqueous solution having suspended therein inert particulate materials having a Knoop hardness of less than 68 which are softer than the outer surface of the teeth.

2. A hygienic slurry according to claim 1 wherein the volumetric ratio of particulate materials to aqueous solution is between about 1:1.5 and 1:10.

3. A hygienic slurry according to claim 2 wherein the diameter of the particulate materials is between about 0.002 and 0.020 inches.

4. A hygienic slurry according to claim 3 wherein the particulate materials are irregular in shape.

5. A hygienic slurry according to claim 3 wherein the volumetric ratio of particulate materials to aqueous solution is between about 1:4 and 1:6.

6. A hygienic slurry according to claim 5 wherein the volumetric ratio of particulate materials to aqueous solution is about 1:5.

7. A hygienic slurry according to claim 5 wherein the aqueous solution contains a breath sweetener.

8. A hygienic slurry according to claim 5 wherein the aqueous solution contains a disinfectant.

9. A hygienic slurry according to claim 5 wherein the aqueous solution contains a fluoridating agent.

10. A hygienic slurry according to claim 5 wherein the particulate material is a plastic.

11. A hygienic slurry according to claim 10 wherein the particulate plastic material is a polyethylene.

12. A hygienic slurry according to claim 10 wherein the particulate plastic material is a polypropylene.

13. A method for cleaning teeth which comprises applying to the surfaces of the teeth at a pressure of about 15 to 60 psi a stream of a slurry comprising an aqueous solution having suspended therein particulate materials having a Knoop hardness of less than 68, which particulate materials are softer than the surfaces of the teeth being cleaned, the ratio of particulate material to aqueous solution in the slurry being between about 1:1.5 and 1:10 and the size of the particulate material being between about 0.002 and 0.020 inches in diameter.

* * * * *